United States Patent
Suh et al.

[19]

[11] Patent Number: 6,027,525
[45] Date of Patent: Feb. 22, 2000

[54] FLEXIBLE SELF-EXPANDABLE STENT AND METHOD FOR MAKING THE SAME

[75] Inventors: Soo Won Suh; In Young Kim; In Wook Choo; Young Soo Do; Sung Wook Choo, all of Seoul, Rep. of Korea

[73] Assignee: Samsung Electronics., Ltd., Kyungki-do, Rep. of Korea

[21] Appl. No.: 08/861,818

[22] Filed: May 23, 1997

[30] Foreign Application Priority Data

| May 23, 1996 | [KR] | Rep. of Korea | 96-17709 |
| Aug. 31, 1996 | [KR] | Rep. of Korea | 96-37394 |
| Sep. 10, 1996 | [KR] | Rep. of Korea | 96-39092 |
| Apr. 3, 1997 | [KR] | Rep. of Korea | 97-12388 |

[51] Int. Cl.$^7$ ........................................................... A61F 2/06
[52] U.S. Cl. ..................................... 623/1; 623/2; 623/12; 623/900
[58] Field of Search ................................ 623/1, 2, 11, 12, 623/900; 606/108, 191, 194, 195, 198

[56] References Cited

U.S. PATENT DOCUMENTS

| 4,086,665 | 5/1978 | Poirier | 623/1 |
| 4,350,492 | 9/1982 | Wright et al. | 623/1 |
| 4,731,073 | 3/1988 | Robinson | 623/1 |
| 5,061,240 | 10/1991 | Cherian | 604/96 |
| 5,104,404 | 4/1992 | Wolff | 623/1 |
| 5,116,564 | 5/1992 | Jansen et al. | 623/2 |
| 5,123,917 | 6/1992 | Lee | 623/1 |
| 5,123,919 | 6/1992 | Sauter et al. | 623/1 |
| 5,314,472 | 5/1994 | Fontaine | 623/1 |
| 5,332,403 | 7/1994 | Kolff | 623/3 |
| 5,500,014 | 3/1996 | Quijano et al. | 623/1 |
| 5,545,211 | 8/1996 | An et al. | 623/1 |
| 5,575,816 | 11/1996 | Rudnick et al. | 623/1 |
| 5,662,713 | 9/1997 | Andersen et al. | 623/12 |
| 5,683,451 | 11/1997 | Lenker et al. | 623/12 |
| 5,733,327 | 3/1998 | Igaki et al. | 623/1 |
| 5,782,904 | 7/1998 | White et al. | 623/1 |
| 5,800,515 | 9/1998 | Nadal et al. | 623/1 |
| 5,891,195 | 4/1999 | Klostermeyer et al. | 623/2 |

FOREIGN PATENT DOCUMENTS

| 1371-700-A | 2/1988 | U.S.S.R. | 623/2 |
| 1593-651-A | 9/1990 | U.S.S.R. | 623/1 |

*Primary Examiner*—Mickey Yu
*Assistant Examiner*—Tram A. Nguyen
*Attorney, Agent, or Firm*—Kile, McIntyre, Harbin & Lee; Eugene M. Lee

[57] ABSTRACT

A flexible self-expandable stent comprises a plurality of radially cylindrical elastic units spaced at fixed intervals, a cylindrical cover fixing member which sheaths the cylindrical elastic units, and a reverse flow preventing valve. The reverse flow preventing valve is attached to the inner wall of the stent, for preventing food-stuffs or fluids from flowing from a downstream side to an upstream side. The flexible self-expandable stent exhibits improved flexibility so that when the stent is disposed in a curved lumina, it can flexibly correspond to the curvature of the lumina and prevent the reverse flow of foodstuffs or fluids by use of the reverse flow preventing valve.

21 Claims, 5 Drawing Sheets

FLEXIBLE SELF-EXPANDABLE STENT AND METHOD FOR MAKING THE SAME

FIELD OF THE INVENTION

The present invention relates to a stent, and more particularly, to a flexible self-expandable stent and a method for making the same which can provide improved flexibility so that when the stent is disposed in curved lumina it can flexibly correspond to curvature of the lumina and prevent the reverse flow of foodstuffs or fluid.

BACKGROUND OF THE INVENTION

Generally, stents are medical devices used to is enlarge lumina of internal organs or blood vessels narrowed by, for example, disease, injury, or surgical operations. Such stents are normally cylindrically shafted and are broadly divided into the following two types: 1) stents having a predetermined amount of elasticity such that they can contract when external force is applied and self-expand when the external force is removed, and 2) stents made of plastic material such that after they are expanded from contracted states, maintain their expanded states.

With regard to the insertion of the above stents in lumina, a widely-used stent insertion device is utilized to allow for easy positioning of the stent. The explanation of this procedure will be omitted herein as this process is well known to those skilled in the art.

U.S. Pat. No. 5,330,500 discloses a stent which, as shown in FIG. 8, comprises a plurality of cylindrical zig-zag elastic units 12, which contract when external force is applied and reexpand when the external force is removed, and a plurality of connecters 13 for connecting the zig-zag elastic units 12 to maintain the same in a cylindrical shape.

Although such a stent utilizing the above zig-zag units 12 attached by the connectors 13 remains in a constant and forceful expanded state, the stent is not flexible nor is it very effective when used to expand lumina which have collapsed. And when used in lumina which are curved in shape, the stent cannot be gently curved, resulting in the zig-zag units 12 and connectors 13 pressing too hard on inside walls of lumina such that inflammation and other complications occur.

Referring to FIG. 9, there is shown a schematic view of another prior art stent positioned in a curved lumen. As shown in the drawing, this stent includes a plurality of zig-zag units 101, a plurality of thread connectors 102 which connect the zig-zag units 101, and a cylindrical cover member 103 made of polyethylene material and which covers the zig-zag units 101 and the connectors 102.

However, the above stent has the drawback of blocking the passageway when used on curved lumina. That is, because the zig-zag units 101 are connected using the thread connectors 102 without any space therebetween and both the zig-zag units 101 and connectors 102 are covered with the cover member 103, when the stent is disposed in a curved lumen, the stent does not gently curve to correspond to a curvature of the lumen, but folds or creases as shown in the drawing so that the passage of the stent, and, thus, the lumen is blocked.

In addition, all prior art stents have the drawback of not having means to prevent the reverse flow of foodstuffs and fluids. Although the human body has natural mechanisms to inhibit the reverse flow of foodstuffs and fluids in the area, for example, where the stomach and esophagus meet, when using the prior art stent in this location it is possible that the esophagus will become damaged because of the reverse flow of acidic foodstuffs and liquids. Further, it is possible that reversed fluid will enter the lungs, leading to lung disease. It is, therefore, not viable to utilize the conventional stent in areas where foodstuffs and liquids need to be prevented from flowing in a reverse direction.

In addition, in the prior stents, the zig-zag units are welded such that each zig-zag unit comes to be formed in a single, integrally formed piece having a plurality of straight sections having a plurality of bends. During the welding process, it is common to use lead material. The lead material, however, can become oxidized within the human body resulting in heavy metals infecting the human body.

SUMMARY OF THE INVENTION

The present invention is made in an effort to solve the above described problems of the prior art.

It is a first object of the present invention to provide a stent which provides improved flexibility so that when it is disposed in curved lumina the stent can follow a curvature of the lumina and not block a passageway of the same.

To achieve the above first object, the present invention provides a stent comprising:

at least a plurality of radially elastic cylindrical units; and a cylindrical cover fixing member for sheathing and fixing the radial elastic cylindrical units without connecting means, wherein the radial elastic cylindrical units are fixed by and disposed on the cylindrical cover fixing member such that adjacent ends of each cylindrical units are spaced at predetermined intervals along the longitudinal axis, and through the flexibility and elasticity of the cylindrical cover fixing member, the expanding and contracting of the cylindrical units is compensated for.

Each of the cylindrical units is designed in a closed zig-zag configuration having a series of straight sections having bends in a cylindrical shape.

Preferably, the cylindrical cover fixing member is made of a material having flexibility and elasticity.

Preferably, the cylindrical cover fixing member is made of polymer materials.

Also preferably, the interval is determined within a range from 0.5I to 1.5I, in which the I is determined according to the following formula, $$I = 2\pi d \frac{\theta}{360} / (\eta - 1)$$

where, I is the interval;

d is a diameter o f the stent;

θ is a curvature angle of the stent; and

η is the number of units.

Further preferably, the interval is selected within a range from 1 mm to 20 mm.

It is a second object of the present invention to provide a stent which, when disposed in lumina, prevents the reverse flow of foodstuffs or fluid so as to prevent the esophagus and lungs from becoming harmed.

To achieve this second object, the stent further comprises a reverse flow preventing means for preventing foodstuffs or fluids from being reversed from a downstream side to an upstream side.

The reverse flow preventing means comprises a trileaflet valve member or a bileaflet valve member which open or close in unison.

Preferably, the reverse flow preventing means includes an opening portion to allow gases to escape therethrough.

Also preferably, the reverse flow preventing means is made of elastic and flexible material Further preferably, the reverse flow preventing means is made of parts from living organisms such as a valve from a pig or a pericardium from a cow.

It is a third object of the present invention to provide a stent which prevents the occurrence of a dangerous situation caused by harmful material, such as lead, entering the human body as in the prior art.

To achieve this object, each of the radially elastic cylindrical units is designed in an opened zig-zag configuration having a series of straight sections being joined by bends in a cylindrical shape, a straight end section of each elastic unit and a second straight end section of each of the radially elastic cylindrical units being adjacent and in contact with each other to provide overlapping end sections.

According to another aspect, the present invention provides a method for making a flexible self-expandable stent, comprising the steps of:

preparing a cylindrical film made of elastic material and having a longitudinal axis;

attaching more than two elastic units having a diameter which is the same as that of the cylindrical elastic film on an outer or inner wall of the cylindrical elastic film, said units being spaced from each other in the longitudinal axis at predetermined intervals;

depositing the cylindrical elastic film and the units with polymer solution; and hardening the deposited solution.

Preferably, the depositing step is performed by soaking the cylindrical elastic film with the units into the polymer solution.

BRIEF DESCRIPTION OF THE DRAWINGS

The accompanying drawings, which are incorporated in and constitute a part of the specification, illustrate an embodiment of the invention, and, together with the description, serve to explain the principles of the invention.

DETAILED DESCRIPTION OF THE PREFERRED EMBODIMENTS

Preferred embodiments of the present invention will now be described in detail with reference to the accompanying drawings.

Figure 1:
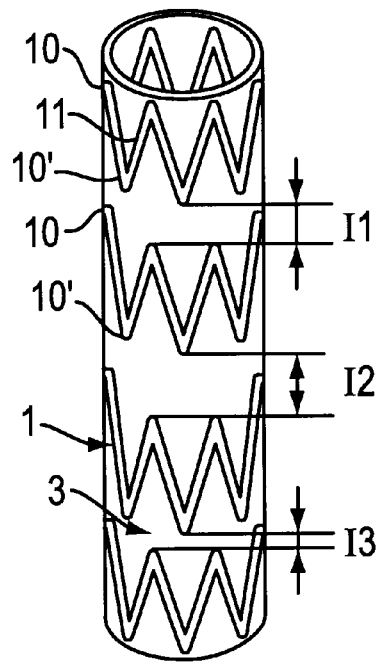
FIG. 1 is a perspective view of a stent according to a preferred embodiment of the present invention.
Figure 2:
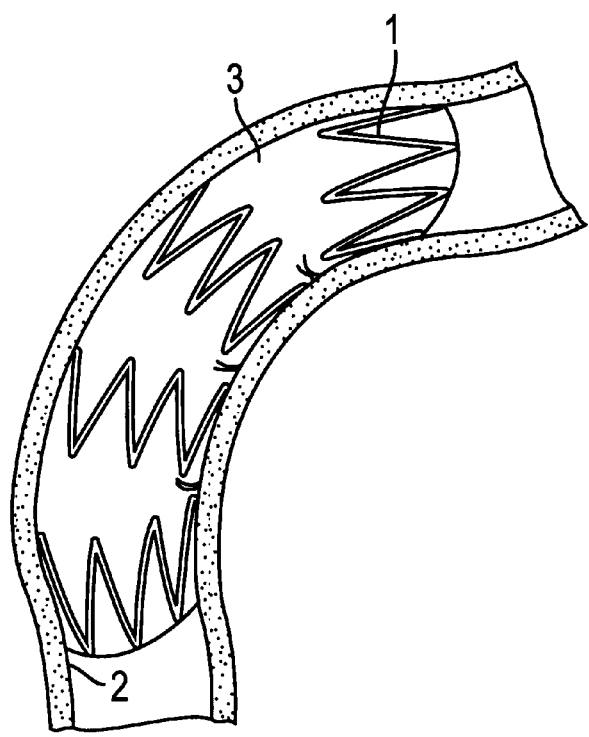
FIG. 2 is a schematic view showing the stent depicted in FIG. 1 applied to a curved lumen.

Referring first to FIGS. 1 and 2, a stent according to a preferred embodiment of the present invention includes a plurality of radially elastic cylindrical units 1, and a cylindrical cover fixing member 3 sheathed over the elastic units 1 to fix the units elastic 1 in a cylindrical shape. That is, the cover fixing member 3 acts as connecting means connecting the elastic units 1 such that separate connecting means, as in the prior art, is unnecessary. Preferably, each of the units 1 has a length is within a range from 10 mm to 20 mm.

The elastic units 1 are covered by the cover fixing member 3 according to the following manner.

A cylindrical elastic film 2 made of elastic material and having a diameter substantially the same as of the elastic units 1 is first prepared. A plurality of elastic units 1 are attached on an outer or inner wall of the elastic film 2. The cylindrical elastic film 2 with the elastic units 1 is then soaked in an elastic material solution which, after drying, completes the forming of the cover fixing member 3 on the elastic units 1. It should be noted, however, that the covering method is not limited to the above process.

The elastic units 1 contract when external force is applied thereon, allowing the stent to be easily inserted within a stent insertion device and expand when the stent insertion device is removed, thereby expanding the lumen. That is, each of the elastic units 1 is made in a zig-zag shape having a series of straight sections 11 having a plurality of upper and lower bends 10 and 10'. The elastic units 1 are fixed by the cylindrical cover fixing member 3 such that the elastic units 1 are spaced apart from each other. Namely, an imaginary circle connecting the lower bends 10' of one elastic unit 1 is spaced from an imaginary circle connecting the upper bends 10 of another adjacent elastic unit 1 in intervals I1, I2 and I3. The intervals I1, I2 and I3 can be identical to, or different from, each other. Since the cylindrical cover fixing member 3 is sheathed over the elastic units 1 such that the cylindrical cover fixing member 3 and the elastic units 1 are integrally formed and take on a cylindrical shape, and the cover fixing member 3 is made of elastic material, the stent can be placed in a curved lumen and easily follow a curvature of the same. As shown in FIG. 2, when the stent according to the present invention is placed in a lumen, the stent is gently curved corresponding to the curvature of the same.

The above is possible because the distance between adjacent upper and lower bends 10 and 10' of each unit 1 at an outer portion of the stent (with respect to the curving direction) enlarges, while the distance between the adjacent upper and lower bends 10 and 10' of each elastic unit 1 at an inner portion of the stent (with respect to the curving direction) decreases. As a result, the stent can be gently curved as shown in FIG. 2.

Therefore, it is preferable to make the cylindrical cover fixing member 3 using polymer material such as polyurethane, polyethylene, polypropylene, polyisoprene, polybutadiene, polychloloprene, or polystyrene, all of which have the elasticity to allow for the above flexibility. The following chart lists the requirements that should be met by the material used for the cover fixing member 3.

| Item | Requirements |
| --- | --- |
| Tensile Modulus | 300–3000 PSI When 50% Extended |
| Ultimate Tensile Strength | Under 4000 PSI |
| Tear Strength | Over 400 Die "c" PSI |
| Flexural Modulus | Under 10,000 PSI |
| Flexural Strength | Under 300 PSI |

Determination of the interval I between adjacent upper and lower bends of adjacent elastic units of the zig-zag type stent according to a preferred embodiment of the present invention will be described hereinafter with reference to FIG. 3.

The interval I is determined using the following formula.

$$I = 2\pi d \frac{\theta}{360} \bigg/ (\eta - 1)$$

where:

d is the diameter of the stent;

θ is the curvature angle of the stent; and

η is the number of units.

The following is the computation method of the above formula.

Figure 3:
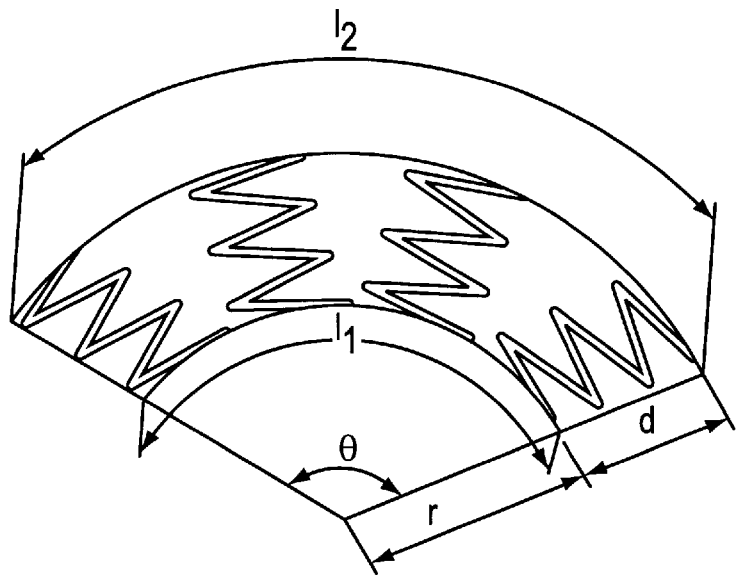
FIG. 3 is a schematic view illustrating spacing between elastic units of the stent shown in FIG. 1.

When the stent is inserted in a curved lumen, the stent comes to be formed having a curvature radius as shown in FIG. 3. It is preferable that the interval I is determined by the difference between a small arc $l_1$ on an inside of the curve, and a large arc $l_2$ on an outside of the curve.

Accordingly, if r is a curvature radius of the small arc, $$l_1 = r\theta \quad (1), \text{ and}$$

$$l_2 = (r+d)\theta \quad (2)$$

If (1) is subtracted from (2), $$l_2 - l_1 = (r+d)\theta - r\theta = d\theta \quad (3)$$

Therefore, the interval I between the zig-zag units 1 is calculated by dividing (3) by the number of folds.

$$I = d\theta/(\eta - 1) \quad (4)$$

As $\theta = 2\pi/360°$, $$S = 2\pi d \frac{\theta}{360} \bigg/ (\eta - 1)$$

The interval I between the zig-zag units 1 calculated using the above formula can be changed ±50% according to the lumina inside which the stent is inserted. That is, the preferable interval range PI which can be applied to the stent of the present invention can be determined as follows:

$$0.5 \times I < PI < 1.5 \times I$$

When using the above formula to determine the interval between adjacent upper and lower bends 10 and 10' of adjacent elastic units 1, manufacturing of the stent is easy and can be done to accurately match the diameter and curvature of lumina.

Figure 4:
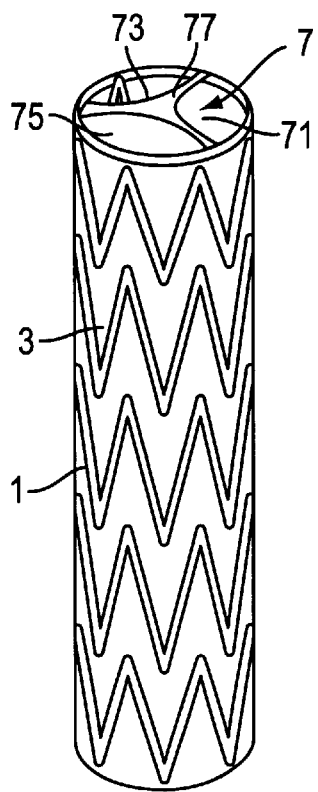
FIG. 4 is a perspective view illustrating a stent where a reverse-flow preventing means according to an embodiment of the present invention is applied.
Figure 5:
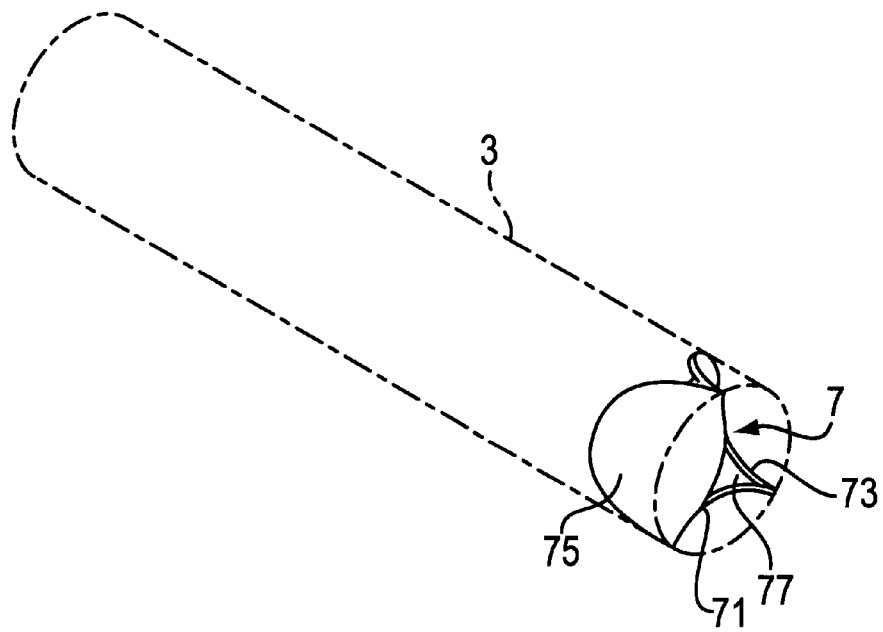
FIG. 5 is a perspective view illustrating the reverse-flow preventing means shown in FIG. 4.

Referring now to FIGS. 4 and 5, there is provided reverse flow preventing means in the stent of the present invention. The reverse flow preventing means 7 is realized through a trileaflet polymer valve.

As shown in FIG. 4, assuming that an upper side of the stent (in the drawing) is upstream and a lower side is downstream, with regard to the direction in which foodstuffs and fluids flow, the reverse flow preventing means 7 is mounted on a downstream end.

The reverse flow preventing means 7 includes three plates 71, 73 and 75. One end and sides of each plate are attached to an inner wall of the stent, while a free end of each plate is progressively positioned toward the center axis of the stent and an attachment area of each plate shares roughly one-third of a circumference of the stent inner wall, a second plate 73. Accordingly, the first, second, and third plates 71, 73 and 75 are adjacent to each other on free ends thereof as shown in the FIGS. 4 and 5.

As a result of the above structure, when foodstuffs or liquids flow from the upstream side to the downstream side by gravity or other forces, the free ends of the plates 71, 73 and 75 are pushed aside such that an opening is created to allow the foodstuffs or liquids to pass therethrough. However, if foodstuffs or liquids flow in the reverse direction (i.e., from downstream to upstream), the free ends of the plates 71, 73 and 75 are pushed together in upstream direction such that a seal is provided to prevent the reverse flow of foodstuffs or liquids.

It is preferable that the plates 71, 73 and 75 are made of a material similar to that used for the cylindrical cover fixing member 3. That is, it is preferable that the plates 71, 73, and 75 are made of polyethylene, polyurethane or other resinous materials such that the material allows the plates 71, 73 and 75 to be freely opened and closed and is not harmful to the human body.

In addition, in the preferred embodiment of the present invention, although the reverse flow preventing means 7 is attached to one end of the stent, it is possible to attach the reverse flow preventing means 7 anywhere along the inside of the stent, and it is also possible to attach the stent protruding outward from an end thereof.

Also, as shown in FIGS. 4 and 5 when the free ends of the plates 71, 73, and 75 are pushed together in the upstream direction, an opening portion 77 is formed between the plates 71, 73 and 75 at approximately the center axis of the stent. The formation of the opening portion 77 is done for allowing gases to escape therethrough when the stent is applied to the area between the stomach and esophagus.

Figure 6:
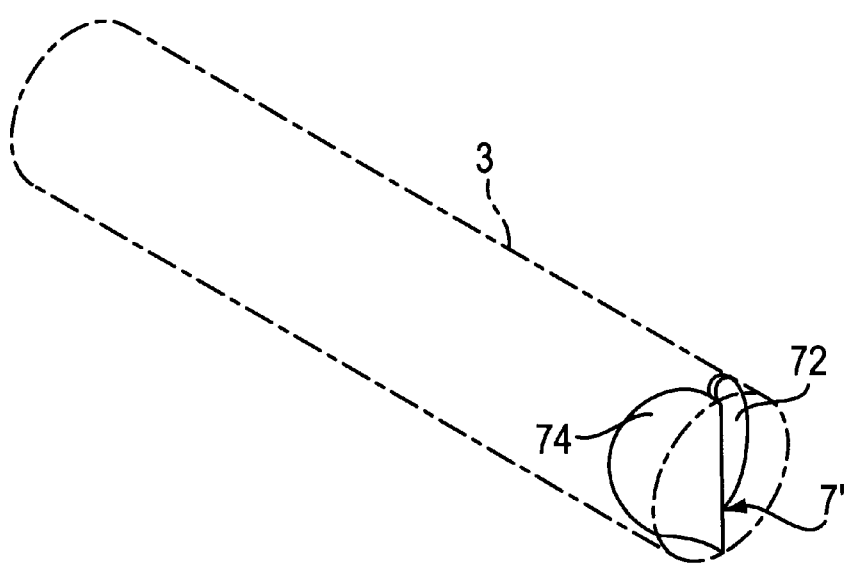
FIG. 6 is perspective view illustrating a reverse-flow preventing means according to another embodiment of the present invention.

Referring now to FIG. 6, there is shown a reverse flow preventing means 7' according to another preferred embodiment of the present invention. The reverse flow preventing means 7 according to this embodiment is realized through a bileaflet polymer valve. As shown in the drawing, the bileaflet polymer valve includes first and second plates 72 and 74. One end and sides of the plates 72 and 74 are attached to the inner wall of the stent while other ends are left unattached and progressively positioned toward the center axis of the stent such that free ends of the plates 72 and 74 come to meet each other.

Previously conventional cylindrical radial elastic units has been made by joining ends of the units by welding using, for example, lead. Therefore, when the stent is placed in lumina, it is possible that harmful material can enter the human body.

Figure 7:
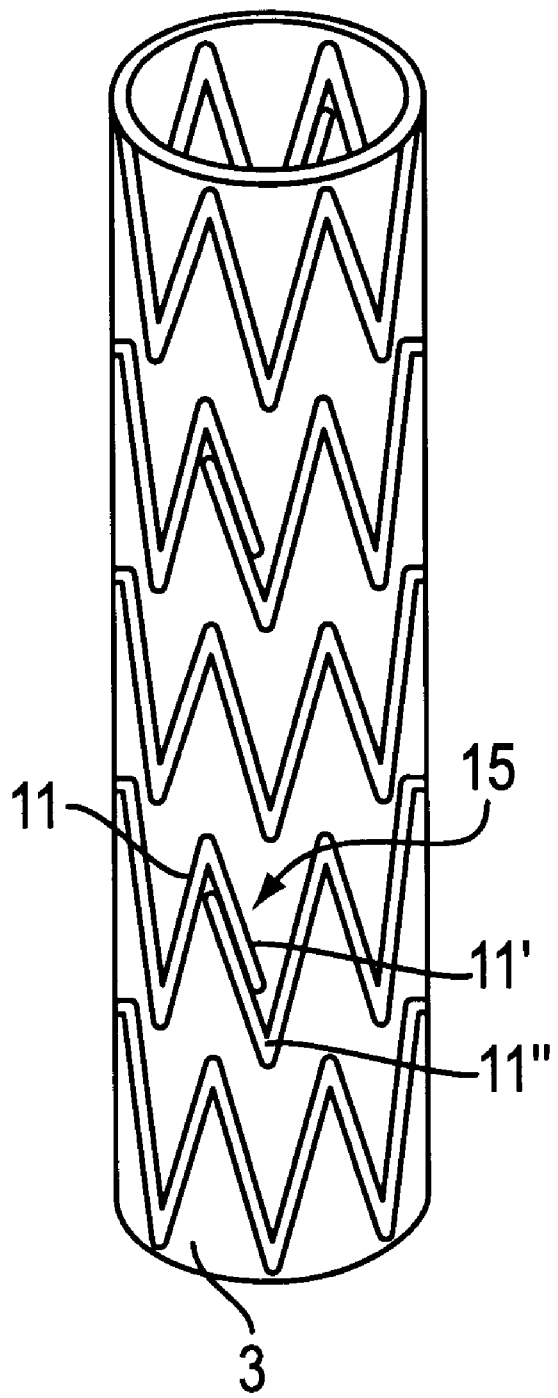
FIG. 7 is a perspective view illustrating a stent according to another embodiment of the present invention.
Figure 8:
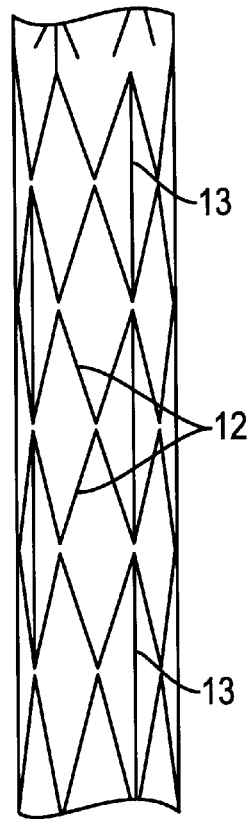
FIG. 8 is a schematic view illustrating a prior stent.
Figure 9:
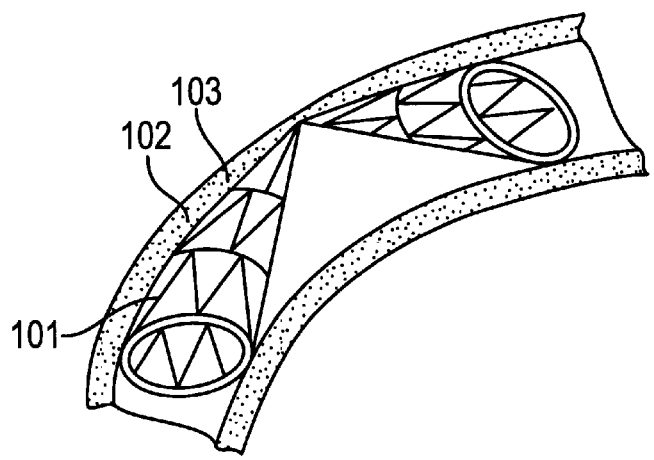
FIG. 9 is a schematic view illustrating another prior stent.

To solve this problem, according to another embodiment of the present invention, the elastic units 11, as shown in FIG. 7, are designed having a zig-zag shape wherein a series of straight sections are joined by bends. That is, one straight end section 11' and the other straight section end 11" of the elastic unit 11 are not joined to each other, but made to contact each other, providing an overlapping portion 15 such that welding is not necessary.

As the reverse flow preventing means is provided in the stent of the present invention, it is possible to safely apply the stent to areas requiring the prevention of the reverse flow of foodstuffs or liquids such as the area between the stomach and esophagus. As a result, medically dangerous situations caused by the reverse-flow of foodstuffs or liquids can be circumvented.

Further, because the present invention provides a stent having improved flexibility, when the stent is disposed in a curved lumina, the scent can follow a curvature of the lumina and not block a passageway of the same.

Finally, as welding is not needed for the elastic units, it is possible to prevent the occurrence of a dangerous situation caused by harmful material, such as lead, entering the human body as in the prior art.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

What is claimed is:

1. A flexible self-expandable stent, comprising:
    a plurality of radially elastic cylindrical units, each of the radially elastic cylindrical units being in an opened zig-zag configuration having a series of straight sections joined by bends in a cylindrical shape, and one straight end section and another straight end section of each of the radially elastic cylindrical units being adjacent and in contact with each other to provide overlapping end sections; and
    a cylindrical cover fixing member for sheathing and fixing the radially elastic cylindrical units;
    wherein the radially elastic cylindrical units are fixed by and disposed on the cylindrical cover fixing member such that adjacent ends of each radially elastic cylindrical unit are spaced at predetermined intervals along the longitudinal axis of the cylindrical cover fixing member.

2. The flexible self-expandable stent according to claim 1, wherein the cylindrical cover fixing member is made of a material having flexibility and elasticity such that the stent may be curved along a longitudinal axis of the stent.

3. The flexible self-expandable stent according to claim 1, wherein the cylindrical cover fixing member is made using a polymer material.

4. The flexible self-expandable stent according to claim 1, wherein the interval between adjacent radially elastic cylindrical units is determined within a range from 0.5 I to 1.5 I, in which I is determined according to the following formula, $$I = 2\pi d \frac{\theta}{360} / (\eta - 1),$$

wherein
    I is the interval between adjacent radially elastic cylindrical units;
    d is a diameter of the stent;
    $\theta$ is a curvature angle of the stent; and
    $\eta$ is the number of radially elastic cylindrical units.

5. The flexible self-expanding stent of claim 4, wherein the interval between adjacent radially elastic cylindrical units is from 1 mm to 20 mm.

6. The flexible self-expanding stent of claim 1, further comprising a reverse flow preventing means for preventing foodstuffs or fluids from flowing from a downstream side to an upstream side, the reverse flow preventing means being attached to an inner wall of the cylindrical cover fixing member and forming an opening portion to allow gases to reversely escape therethrough.

7. The flexible self-expanding stent of claim 6, wherein the reverse flow preventing means comprises a trileaflet valve member.

8. The flexible self-expanding stent of claim 7, wherein the trileaflet valve member includes three plates, one end and sides of each plate being attached to an inner wall of the stent, a free end of each plate being progressively positioned toward a center axis of the stent.

9. The flexible self-expandable stent according to claim 6, wherein the reverse flow preventing means comprises a bileaflet valve member.

10. The flexible self-expandable stent according to claim 9, wherein the bileaflet valve member includes two plates, one end and sides of each plate being attached to an inner wall of the stent, and a free end of each plate being progressively positioned toward a center axis of the stent.

11. The flexible self-expandable stent according to claim 6, wherein the reverse flow preventing mean is made of parts from living organisms including a valve from a pig or a pericardium from a cow.

12. A flexible self-expandable stent, comprising:
    a plurality of radially elastic cylindrical units, each of the radially elastic cylindrical units being in an opened zig-zag configuration having a series of straight sections joined by bends in a cylindrical shape, and one straight end section and another straight end section of each of the radially elastic cylindrical units being adjacent and in contact with each other to provide overlapping end sections;
    a cylindrical cover fixing member for sheathing and fixing the radially elastic cylindrical units; and
    a reverse flow preventing means for preventing foodstuffs or fluids from flowing from a downstream side to an upstream side, the reverse flow preventing means being attached to an inner wall of the cylindrical cover fixing member and forming an opening portion to allow gases to reversely escape therethrough,
    wherein the radially elastic cylindrical units are fixed by and disposed on the cylindrical cover fixing member such that adjacent ends of each radially elastic cylindrical unit are spaced at predetermined intervals along the longitudinal axis of the cylindrical cover fixing member.

13. The flexible self-expandable stent according to claim 12, wherein the cylindrical cover fixing member is made of a material having flexibility and elasticity such that the stent may be curved along a longitudinal axis of the stent.

14. The flexible self-expandable stent according to claim 12, wherein the cylindrical cover fixing member is made using a polymer material.

15. The flexible self-expandable stent according to claim 12, wherein the interval between adjacent radially elastic cylindrical units is determined within a range from 0.5 I to 1.5 I, in which I is determined according to the following formula, $$I = 2\pi d \frac{\theta}{360} / (\eta - 1),$$

wherein
    I is the interval between adjacent radially elastic cylindrical units;
    d is a diameter of the stent;
    $\theta$ is a curvature angle of the stent; and
    $\eta$ is the number of radially elastic cylindrical units.

16. The flexible self-expanding stent of claim 15, wherein the interval between adjacent radially elastic cylindrical units is from 1 mm to 20 mm.

17. The flexible self-expanding stent of claim 12, wherein the reverse flow preventing means comprises a trileaflet valve member.

18. The flexible self-expanding stent of claim 17, wherein the trileaflet valve member includes three plates, one end and sides of each plate being attached to an inner wall of the stent, a free end of each plate being progressively positioned toward a center axis of the stent.

19. The flexible self-expandable stent according to claim 12, wherein the reverse flow preventing means comprises a bileaflet valve member.

20. The flexible self-expandable stent according to claim 19, wherein the bileaflet valve member includes two plates, one end and sides of each plate being attached to an inner wall of the stent, and a free end of each plate being progressively positioned toward a center axis of the stent.

21. The flexible self-expandable stent according to claim 12, wherein the reverse flow preventing means is made of parts from living organisms including a valve from a pig or a pericardium from a cow.

* * * * *